(12) United States Patent
Kim et al.

(10) Patent No.: US 8,977,331 B2
(45) Date of Patent: Mar. 10, 2015

(54) SYSTEMS AND METHODS FOR NERVE IMAGING

(71) Applicant: General Electric Company, Schenectady, NY (US)

(72) Inventors: Evgenia Mikhailovna Kim, Ballston Lake, NY (US); Siavash Yazdanfar, Niskayuna, NY (US); Cristina Abucay Tan Hehir, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 272 days.

(21) Appl. No.: 13/713,745

(22) Filed: Dec. 13, 2012

(65) Prior Publication Data

US 2014/0171764 A1 Jun. 19, 2014

(51) Int. Cl.
*A61B 5/00* (2006.01)
*A61B 17/00* (2006.01)
*A61B 1/00* (2006.01)
*A61B 1/04* (2006.01)
*A61B 1/06* (2006.01)

(52) U.S. Cl.
CPC .............. *A61B 5/0071* (2013.01); *A61B 17/00* (2013.01); *A61B 5/4893* (2013.01); *A61B 1/00009* (2013.01); *A61B 1/043* (2013.01); *A61B 1/0638* (2013.01); *A61B 5/6847* (2013.01); *A61B 2505/05* (2013.01); *A61B 2576/02* (2013.01)
USPC ............ 600/317; 600/476; 600/477; 382/128

(58) Field of Classification Search
USPC .................. 600/317, 473, 476, 477; 382/128
See application file for complete search history.

(56) References Cited

U.S. PATENT DOCUMENTS

| | | | |
|---|---|---|---|
| 4,791,310 | A | 12/1988 | Honig et al. |
| 5,719,063 | A | 2/1998 | Block |
| 6,272,376 | B1 | 8/2001 | Marcu et al. |
| 6,537,829 | B1 | 3/2003 | Zarling et al. |

(Continued)

FOREIGN PATENT DOCUMENTS

WO      2008089545 A1     7/2008

OTHER PUBLICATIONS

Whitney et al., "Fluorescent Peptides Highlight Peripheral Nerves During Surgery in Mice", Letters, Nature Biotechnology, vol. 29, No. 4, Apr. 2011, pp. 352-358.

(Continued)

*Primary Examiner* — Michael Rozanski
(74) *Attorney, Agent, or Firm* — Scott J. Asmus

(57) ABSTRACT

Systems and methods for imaging are presented. The method includes producing excitation light configured to induce fluorescence in an imaging agent that selectively binds to a target species in a region of interest (ROI) of a subject that also includes a background species. A first and a second spectral region are selected such that a determined difference between fluorescence corresponding to the target and the background species in the first spectral region differs from a corresponding difference in the second spectral region. First and second fluorescence images are generated from the fluorescence corresponding to the first and second spectral regions. Additionally, a fluorescence ratio for the background species in the first and second fluorescence image is determined. The first fluorescence image is then multiplied or divided with the determined ratio to generate an intermediate image that is subtracted from the second fluorescent image to reconstruct a background-subtracted image.

16 Claims, 10 Drawing Sheets

(56) References Cited

U.S. PATENT DOCUMENTS

| | | |
|---|---|---|
| 8,031,924 B2 | 10/2011 | Can et al. |
| 8,169,696 B2 | 5/2012 | Yazdanfar et al. |
| 2010/0220903 A1 | 9/2010 | May et al. |
| 2010/0310456 A1 | 12/2010 | Siclovan et al. |
| 2010/0310457 A1 | 12/2010 | Tan Hehir et al. |
| 2011/0087111 A1 | 4/2011 | Ntziazhristos et al. |
| 2011/0142759 A1 | 6/2011 | Zhang et al. |
| 2012/0045848 A1 | 2/2012 | Haugland et al. |
| 2012/0100560 A1 | 4/2012 | Searson et al. |

OTHER PUBLICATIONS

Winterer et al., "Direct Monitoring of Vesicular Release and Uptake in Brain Slices by Multiphoton Excitation of the Styryl FM 1-43", Research Report, Biotechniques, vol. 40, Issue 3, Mar. 2006, pp. 343-351.

Themelis et al., "Real-time intraoperative fluorescence imaging system using light-absorption correction", Journal of Biomedical Optics, vol. 14(6) 064012 Nov./Dec. 2009, 9 Pages.

Robert Gates, Elner Rathbone, Lisa Masterson, Ian Wright, Asgar Electricwala.; Glycoprotein Analysis Manual; 1st Edition, sigma-aldrich.com; 87 Pages.

SYSTEMS AND METHODS FOR NERVE IMAGING

STATEMENT OF GOVERNMENT INTEREST

This invention was made with government support under R01 EB011872 awarded by National Institutes of Health through the National Institute of Biomedical Imaging and Bioengineering. The government has certain rights in the invention.

BACKGROUND

Embodiments of the present disclosure relate generally to fluorescence imaging, and more particularly to systems and methods for suppression of background species during nerve imaging.

Surgical procedures, including laparoscopic studies and interventions, are prone to cause iatrogenic nerve damage, which in turn, may lead to loss of function, loss of sensation, muscle atrophy and/or chronic neuropathy in a patient. Often, such damage is caused inadvertently during surgery due to poor visibility of a target species, for example nerves, in comparison to surrounding tissues. Accordingly, certain imaging systems employ anatomical landmark identification for imaging the target species. Certain other systems use optical imaging for microscopic and/or macroscopic visualization of the target species. For example, in recent times, systems employing fluorescence image guided surgery have been used for visualizing nerves and other critical structures during surgery.

Particularly, fluorescence imaging allows highlighting of biological molecules and structures by providing greater contrast and visualization of these structures to a clinician during surgery and/or endoscopy. To that end, a fluorescence agent (fluorophore) may be administered to a patient for targeted labeling of diseased structures, such as cancerous tumor margins) and/or for labeling of critical anatomical structures such as nerves or the ureter for visualization during clinical examination and/or surgery. Although the fluorophores are designed to label a particular species, for example nerves or tumor margins, nonspecific or competitive binding of the fluorophores may result in poor signal-to-background ratio (SBR) and/or limited dynamic range. Accordingly, many bright fluorophores that specifically label biological targets and have favorable biological and chemical properties may be eliminated from the development pipeline due to inadequate SBR, thus resulting in a dearth of efficient fluorophores.

Certain imaging systems, thus, have sought to use more efficient algorithms and/or acquisition protocols for improved fluorescent imaging. One conventional imaging system operating in the near-infrared spectrum, for example, describes use of a normalized fluorescence method that corrects for attenuation heterogeneity across a tissue surface. Specifically, the normalized fluorescence method employs a ratio-based correction, which corrects for measurements at the emission (fluorescence) wavelength. Typically, the corrections are made by dividing the measurements with geometrically identical light attenuation measurements in tissue at the same or similar wavelengths such as at the excitation wavelength.

Although, such conventional approaches may allow generation of fluorescence images indicative of spatially varying absorption in the imaged tissue, such approaches still fail to provide significant improvement in suppressing unintentionally labeled background tissues, while allowing for reliable identification of target biological tissues during imaging.

BRIEF DESCRIPTION

In accordance with certain exemplary aspects of the present disclosure, an imaging system is disclosed. The system includes one or more illumination sources configured to produce excitation light that induces fluorescence emissions in an imaging agent configured to bind to a target species in a region of interest of a subject that further includes a background species. The system further includes at least one beam splitter configured to separate the fluorescence emissions into a first spectral region and a second spectral region, where a determined difference between fluorescence corresponding to the target species and the background species in the first spectral region differs from a corresponding difference in the second spectral region. The system also includes one or more signal detectors configured to collect fluorescence emissions corresponding to the first spectral region and the second spectral region. Additionally, the system includes a processing unit operatively coupled to the one or more signal detectors. The processing unit is configured to generate a first fluorescence image from the fluorescence emissions corresponding to the first spectral region and a second fluorescence image from the fluorescence emissions corresponding to the second spectral region. Further, the processing unit determines a ratio of fluorescence corresponding to the background species in the first fluorescence image and the second fluorescence image. The processing unit then multiplies or divides the first fluorescence image with the determined ratio to generate an intermediate image. Subsequently, the processing unit reconstructs a background-subtracted image by subtracting the intermediate image from the second fluorescence image.

In accordance with certain other aspects of the present disclosure, a system for nerve imaging is presented. The system includes one or more illumination sources configured to produce at least a first excitation wavelength and a second excitation wavelength for inducing fluorescence emissions in an imaging agent, where the imaging agent selectively binds to a target species in a region of interest of a subject that further includes a background species. Particularly, the first excitation wavelength and the second excitation wavelength are selected such that a determined difference between fluorescence corresponding to the target species and the background species emitted in response to the first excitation wavelength differs from a corresponding difference in fluorescence emitted in response to the second excitation wavelength. The system further includes one or more signal detectors configured to collect the fluorescence emitted in response to the first excitation wavelength and the second excitation wavelength. Additionally, the system also includes a processing unit operatively coupled to the one or more signal detectors. The processing unit is configured to generate a first fluorescence image from the fluorescence emitted in response to the first excitation wavelength and a second fluorescence image from fluorescence emitted in response to the second excitation wavelength. Further, the processing unit determines a ratio of fluorescence corresponding to the background species in the first fluorescence image and the second fluorescence image. The processing unit then multiplies or divides the first fluorescence image with the determined ratio to generate an intermediate image. Subsequently, the processing unit reconstructs a background-subtracted image by subtracting the intermediate image from the second fluorescence image.

In accordance with certain further aspects of the present disclosure, a method for imaging is disclosed. The method includes producing excitation light configured to induce fluorescence emissions in an imaging agent that selectively binds to a target species in a region of interest of a subject, where the region of interest comprises the target species and a background species. Further, a first spectral region and a second spectral region are selected such that a determined difference between fluorescence corresponding to the target species and the background species in the first spectral region differs from a corresponding difference in the second spectral region. Subsequently, a first fluorescence image is generated from the fluorescence emissions corresponding to the first spectral region and a second fluorescence image is generated from the fluorescence emissions corresponding to the second spectral region. Additionally, a ratio of fluorescence corresponding to the background species in the first fluorescence image and the second fluorescence image is determined. The first fluorescence image is multiplied or divided with the determined ratio to generate an intermediate image. Further, a background-subtracted image is reconstructed by subtracting the intermediate image from the second fluorescent image.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The following description presents system and methods for fluorescence imaging for use in open and/or minimally-invasive surgical (MIS) procedures. Particularly, certain embodiments illustrated herein describe efficient methods and systems that provide significant improvement in suppressing unintentionally labeled background tissues, while allowing for reliable identification of targeted biological tissues during fluorescence imaging.

For discussion purposes, embodiments of the present system are described with reference to an optical imaging system configured to generate high quality fluorescence images for visualizing a target species, for example, nerves. However, in certain other embodiments, the present system may include any other suitable imaging device such as a laparoscope or a hand-held device configured to image other targeted species such as tumor margins based on specific implementation requirements. An exemplary environment that is suitable for practicing various implementations of the present systems and methods are described in the following sections with reference to FIGS. 1A and 1B.

Figure 1A:
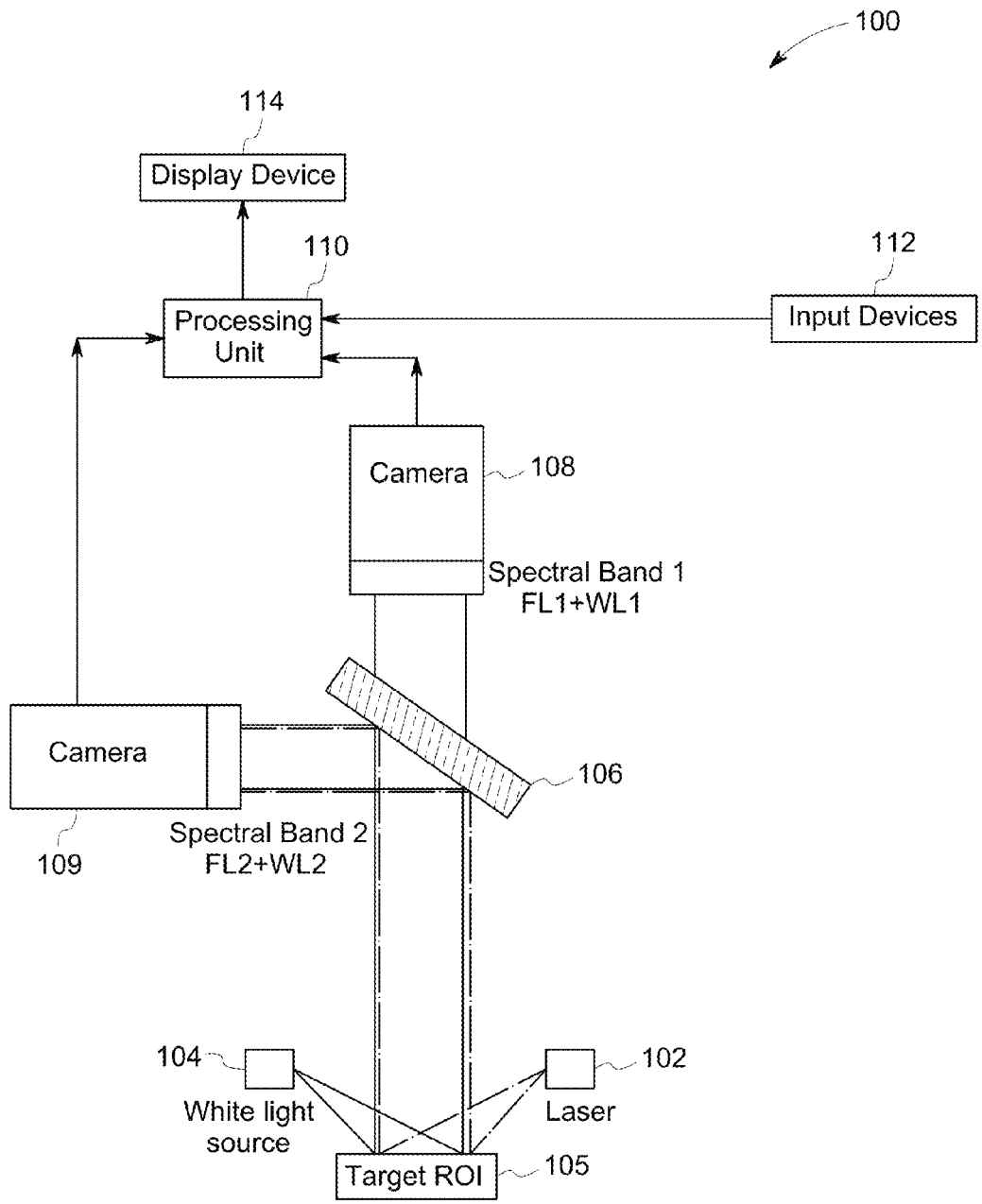
FIGS. 1A and 1B are schematic representations of exemplary embodiments of imaging systems for generating high quality fluorescence and/or white light images, in accordance with aspects of the present disclosure.
Figure 1B:
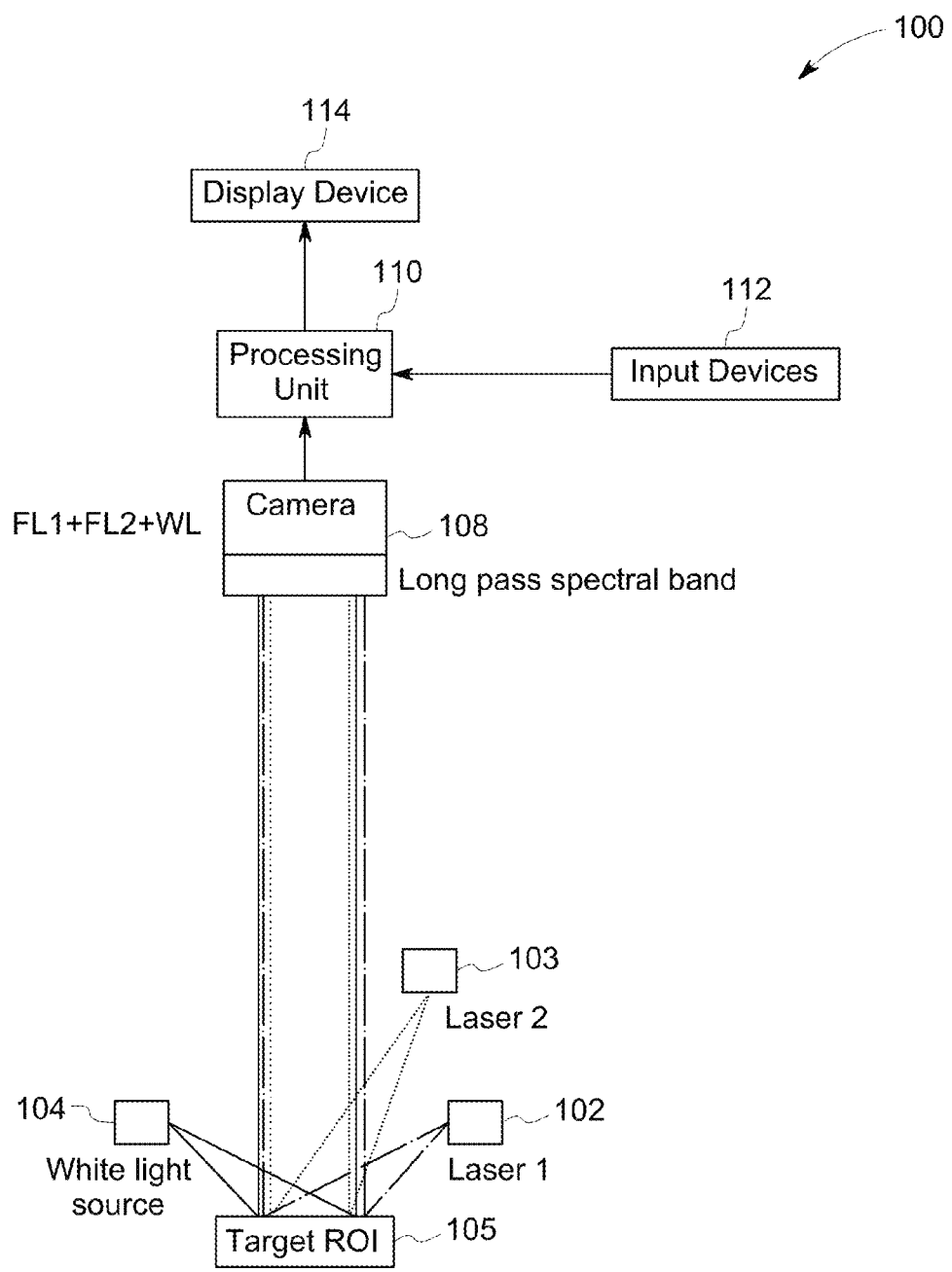

FIGS. 1A and 1B illustrate different embodiments of an exemplary imaging system 100 for generating high quality fluorescence and/or color images. As previously noted, fluorescence imaging may be used to highlight molecules and structures of interest during surgeries and/or endoscopy. Particularly, in concert with white light imaging, fluorescence imaging captures movies of anatomy with tissue specific information and provides a clinician with a macroscopic visualization of biology in its intact and native physiological state. Fluorescence imaging, thus, may allow for generation of images that may provide real time guidance during various medical procedures such as tumor resection, sentinel lymph node mapping, vasculature and tissue perfusion imaging, as well as early detection of colorectal, lung and esophagus cancer.

To that end, in one embodiment, a targeted nerve imaging agent that selectively binds, for example, to myelin basic protein (MBP) in the nerve tissues may be used for fluorescence guided surgical imaging of nerves. Many of the common surgical sites such as heart and breast regions include a number of myelinated nerves. Further, clinically important motor and sensory nerves, such as the anterior intercostal nerve as well as the nerves innervating the prostate are myelinated. Improved visualization of the nerve tissues by use of a targeted nerve imaging agent that specifically binds to MBP, thus, may aid in reducing iatrogenic nerve damage by providing better visualization of nerves and/or more accurate guidance, both during open surgeries such as cardiovascular and breast cancer surgeries and during minimally-invasive procedures.

Myelin, however, is a complex mixture composed of approximately about 80% lipid fraction and about 20% protein fraction. MBP is a major component of myelin at about 5%-15%, which translates into about 5 millimolar (mM) target concentration and satisfies the abundance criterion. Typically, conventional imaging agents need to be lipophilic to allow for penetration into the blood nerve barrier. Certain conventional imaging agents, thus, may bind to unintentionally labeled adipose tissue as well as targeted nerve tissue in the target ROI, which in turn, may result in incorrect identification, further leading to iatrogenic damage. Thus, there is a need to discriminate between adipose and nerve fluorescence intraoperatively.

Accordingly, certain aspects of the present disclosure allow for use of targeted nerve imaging agents (fluorophores) that exhibit target abundance, high binding affinity and selectivity to the target, and an ability to penetrate the blood nerve barrier. To that end, the nerve imaging agents may be applied to the surgical site, for example, using intravenous, intraperitoneal, subcutaneous, intramuscular, intrathecal, intracerebral, intracerebroventricular, topical, and/or intraspinal injections. Certain exemplary nerve imaging agents for use in suppression of nonspecifically labeled species during nerve imaging in accordance with exemplary aspects of the present disclosure have been described in more detail in patent applications US 2010/0310456A1, US 2010/0310457A1, and US 2011/0142759A1, which are herein incorporated in their entirety.

More specifically, in one non-limiting embodiment, the targeted nerve imaging agent for use in visualizing structures of interest in a target region includes, for example, a compound of Formula I,

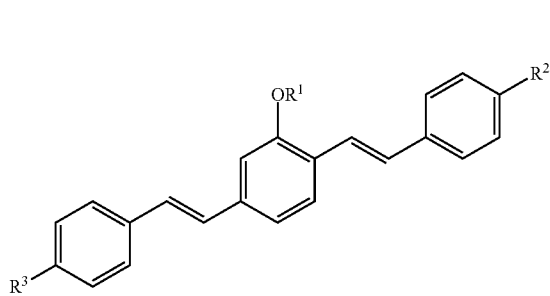

where $R^1$ corresponds to an alkyl group, $R^2$ corresponds to an electron donating group and $R^3$ corresponds to an electron withdrawing group. Alternatively, $R^2$ may correspond to an electron withdrawing group, whereas $R^3$ corresponds to an electron donating group.

In certain embodiments R1 may be a lower alkyl group of about 1 to 6 carbon atoms, preferably about 1 to 4 carbon atoms, and further including methyl, ethyl, n-propyl, isopropyl, and n-, s- and t-butyl.

Further, as used herein, the term "Electron donating group" refers to chemical groups that add electron density to the conjugated π system making it more nucleophilic. Electron donating groups may be recognized by lone pairs of electrons on an atom adjacent to the π system. Examples of electron donating groups include, but are not limited to, —NR'R", —NHR, —NH$_2$, —NC(NH$_2$)$_2$, —OH, —OR, —SR, —NH-COR, —OCOR, —C$_6$H$_5$, and —CH=CR$_2$.

Moreover, as used herein, the term "Electron withdrawing group" refers to chemical groups that remove electron density from the conjugated π rendering the structure less nucleophilic. Electron withdrawing groups may be recognized either by the atom adjacent to the π system having several bonds to more electronegative atoms or, having a formal positive charge. Examples of electron withdrawing groups include, but are not limited to, —CHO, —COR, —COOR, —COOH, —CONH$_2$, —CONHR, —CONR$_2$, —CF$_3$, —CN, C=C(CN)$_2$—SO$_3$H, —NH$_3$+, —NR$_3$+, —NO$_2$, —SOR, —SO$_2$R, —SO$_2$NH$_2$, —SO$_2$NHR, and —SO$_2$NR$_2$.

In one embodiment, R2 and R3 may be conjugated through the π double bond orbitals of the benzene rings and olefinic substituents, thus providing a clear path for electrons to flow from the electron-donating group to the electron-withdrawing group. The electron-donating group may be in the R2 or R3 position, as illustrated in Formula I, provided that an electron-withdrawing group is in the alternative position. This conjugation and "push-pull" electron flow from R2 to R3, as well as R2 to —SO2R4 may be responsible for a Stokes shift of a longer wavelength during fluorescence as compared to similar heterocyclic compounds, thus, allowing for enhanced contrast between myelin and surrounding tissue.

Although a presently contemplated embodiment describes the use of the compound of Formula I, certain other embodiments may use other targeted imaging agents that improve visualization of the target species and/or minimize background autofluorescence (for example. due to collagen, elastin, Nicotinamide Adenine Dinucleotide plus Hydrogen (NADH)), tissue scattering and/or absorption. Additionally, in one embodiment, absorption and emission of the MBP nerve imaging agent may be shifted to the near infrared (NIR) fluorescence region to minimize interference from autofluorescence and maximize depth penetration. In certain other embodiments, however, absorption and emission of the MBP nerve imaging agent may correspond to the visible fluorescence region. Certain embodiments of the present disclosure may entail inducing fluorescence in the MBP nerve imaging agent for generating high quality fluorescence and/or color images, for example, using the exemplary systems illustrated in FIGS. 1A and 1B.

Particularly, FIG. 1A illustrates an exemplary configuration of an imaging system 100 with one excitation light source 102 and two emission channels for fluorescence imaging. The system 100, in certain embodiments, may also include a white light source 104 for use in white light imaging. In one embodiment, the source 102 may be configured to produce excitation light for imaging a target region of interest (ROI) 105 of a subject, such as a patient. To that end, the source 102, for example, may include high power lamps, diode lasers and/or light-emitting diodes (LED) configured to produce excitation light for inducing fluorescence in an imaging agent that selectively binds to a target species in the ROI of the patient. Further, the white light source 104, for example, may include a lamp or an LED of a designated power.

In one embodiment, the system 100 may use the fluorescence images for discriminating between nerve and adipose tissues, for example, through spectral unmixing and/or ratiometric imaging. To that end, in certain embodiments, the system 100 may be configured to image the target ROI 105 using a single fluorescence illumination source 102 configured to produce excitation light capable of inducing fluorescence in the MBP imaging agent. In one embodiment, the system 100 may further include optical elements such as a beam splitter 106 configured to separate the emitted fluorescence into at least a first spectral region and a second spectral region. Accordingly, the optical elements, for example, may include one or more dichroic filters and/or prisms configured to selectively transmit light of one or more desired wavelengths emitted from the surgical site. Particularly, in one embodiment, the dichroic beam splitter may be configured to separate fluorescence emissions into specific wavelengths corresponding to the first and second spectral regions for detection.

In certain embodiments, the first and the second spectral regions may be selected, for example, using equation (1):

$$T1-B1 \neq T2-B2 \qquad (1)$$

where T1 corresponds to fluorescence of the target species in the first spectral region, B1 corresponds to fluorescence of the background species in the first spectral region, T2 corresponds to fluorescence of the target species in the second spectral region and B2 corresponds to fluorescence of the background species in the second spectral region.

Accordingly, in the embodiment illustrated in FIG. 1A, the dichroic beam splitter 106 is selected such that the beam splitter 106 separates the fluorescence emissions into the first and second spectral regions based on equation (1). Although the embodiment illustrated in FIG. 1A depicts a single beam splitter 106, in certain embodiments, the system 100 may include more than one beam splitter.

Additionally, the system 100 may also include other optical devices for example, optical filters such as a laser rejection filter, an emission filter and/or a notch filter, lens and/or focus and iris adjustments means (not shown) configured via manual and/or automated controls to direct the excitation light and fluorescence emissions through a designated optical path for detection. For example, the system 100 may employ various lens designs including, but not limited to, telephoto, retrofocus, afocal zoom lens and/or optical compensated Pan-Cinor zoom lens for optimizing collection efficiency. Moreover, the lens may be configured for varying entrance pupil diameter (EPD) high zoom ratio and correction for spherical, chromatic, astigmatism, coma, field curvature and other aberrations for generating high-contrast images from signals corresponding to the resulting fluorescence emissions.

Moreover, in one embodiment, the system 100 may include a plurality of signal detectors 108-109 configured to collect the fluorescence emissions corresponding to the first spectral region and the second spectral region from first and second emission channels, respectively. In certain embodiments, where the system 100 includes the white light source 104, the detectors 108-109 may be configured to collect corresponding white light signals reflected from the target ROI 105 in at least one of the emission channels, for example, using time-domain multiplexing. In certain embodiments, the system 100 may be configured such that a time-domain multiplexing of the detectors 108-109, the white light source 104 and the fluorescence excitation light source 102 may be employed on both emission channels, in accordance with aspects of the present disclosure.

Accordingly, in one embodiment, the detectors 108-109 may include a lightweight and sensitive CCD array detector configured to employ a time-domain multiplexing of the available emission channels. In another embodiment, the detectors 108-109 may include a compact, actively cooled, electron-multiplying charge coupled device (EMCCD) camera. Other suitable cameras include complementary metal-oxide-semiconductor (CMOS) and scientific CMOS cameras. Additionally, in certain embodiments, the detectors 108-109 may be externally triggered, for example, at twice the frequency of a light source trigger to allow continuous recording of white light and fluorescence images. Furthermore, in certain implementations, where a fluorescence mode of operation may produce a lower signal level as compared to a white light detection (RBG range) mode, one or more parameters of the detectors 108-109 may be adjusted to selectively improve fluorescence detection sensitivity and/or detector gain.

Further, in one embodiment, the fluorescence emissions corresponding to the first and second spectral regions collected from the first and second emission channels may be transmitted to a processing unit 110. Particularly, the processing unit 110 may be configured to process the received signals to allow generation of, for example, fat-suppressed images in real-time for use during surgical procedures. To that end, the processing unit 110, for example, may include one or more application-specific processors, graphical processing units (GPUs), digital signal processors (DSPs), microcomputers, microcontrollers, Application Specific Integrated Circuits (ASICs) and/or Field Programmable Gate Arrays (FPGAs).

Often during imaging, imaging agents may bind to a background species different from an intended target species in the target ROI 105. For example, although the MBP imaging agent may be targeted to bind to nerve tissues, certain adipose or fat tissues may also be labeled due to a lipophilic nature of the MBP agent. Accordingly, the signals received from the first and second emission channels may include erroneous imaging data that may lead to incorrect image reconstruction. During surgical procedures, a medical practitioner typically relies on image-derived parameters to distinguish between healthy and pathological tissue types. Use of incorrect and unreliable images, thus, may lead to inaccurate diagnosis, incorrect treatment and/or result in iatrogenic damage to patient tissues.

Accordingly, embodiments of the present disclosure allow for processing of the fluorescence emissions corresponding to the first and second spectral regions by the processing unit 110 for reliable identification of imaging data corresponding to unintentionally labeled background species, for example, fat tissues. The processing unit 110 may then use the identification information to improve visualization of the target species, for example nerves, by suppressing the fat tissues in the resulting background-subtracted images.

To that end, in one embodiment, the processing unit 110 may be configured to generate first and second raw fluorescence images from the emissions corresponding to the first and second spectral regions, respectively. Further, the unintentionally labeled fat tissues common to both the first and second raw fluorescent images may be identified. In one example, the fat tissues may be identified using an automated analysis of the first and second raw fluorescence images. Alternatively, the fat tissues may be identified based on user input received via one or more input devices 112 operatively coupled to the processing unit 110. The input devices, for example, may include a keyboard, touchscreen, microphone, mouse, buttons and/or switches for receiving commands and inputs from an operator, for example, to identify the target ROI, the background species, the target species and/or other imaging information. The processing subsystem 100 may also allow the operator to make selections, for example, using a graphical user interface (GUI) on a local or remote display device 114 communicatively coupled to the processing unit 110.

Once the fat tissues are identified, the processing unit 110 may determine a ratio of fluorescence corresponding to the fat tissues in the first and the second fluorescence images. Further, the processing unit 110 may multiply or divide the first fluorescence image with the determined ratio to generate an intermediate fat-equalized image that may then be subtracted from the second fluorescence image to reconstruct a high quality fat-suppressed image. In embodiments where the system 100 includes use of white and/or visible light, the processing unit 110 may also reconstruct, for example, an anatomic image and/or color video of the target ROI 105.

The processing unit 110 may transmit one or more of such fat-suppressed images and/or video to the display device 114, for example, for use in fluorescence image guided surgery. Accordingly, in certain embodiments, the processing unit 110 may allow co-registration of the anatomic image with fat-suppressed fluorescence images in real time for display over a common spatial coordinate system. The medical practitioner may use one or more of such fat-suppressed images for making an accurate assessment of the pathological condition of the patient and/or for carefully guiding surgical devices through the patient anatomy in real-time.

It may be noted that FIG. 1A illustrates a specific embodiment of the system 100 with certain exemplary components for use in generating fluorescence and/or visible images. Other embodiments, however, may include different configurations of the system 100 including fewer or more components than those illustrated in FIG. 1A. FIG. 1B, for example, illustrates an alternative embodiment of the system 100 using single emission and multiple excitation approach for generating high fidelity fat-suppressed images. To that end, that system 100 may employ a single camera or detector 108 for collecting white light and/or fluorescence emissions. The system 100 further may include at least two fluorescence illumination sources 102 and 103 configured to produce multiple excitations for producing corresponding fluorescence emissions.

In one embodiment, the source 102 may be a laser diode configured to produce a first excitation wavelength, whereas the source 103 may be another light source configured to produce a second excitation wavelength. In certain embodiments, at least two excitation wavelengths are selected, for example, using equation (1). Particularly, the two excitation wavelengths may be selected such that a determined difference between fluorescence corresponding to the target species and the background species emitted in response to the first excitation wavelength differs from a corresponding difference in fluorescence emitted in response to the second excitation wavelength. Accordingly, in the embodiment illustrated in FIG. 1B, the system 100 may not include a dichroic beam splitter such as illustrated in the embodiments of FIG. 1A. Instead, the system 100 may employ time-domain multiplexing to allow the detector 108 to collect the fluorescence emissions corresponding to the first and the second excitation wavelengths in a time-interleaved manner from alternating frames.

In certain embodiments, the system 100 may further include the white light source 104 such as an LED for imaging the target ROI 105. Accordingly, the system 100 may employ time-domain multiplexing of the single emission channel to collect the fluorescence emissions corresponding to the first and the second excitation wavelengths, and white light, alternately one after the other in three consequent frames. To that end, in one embodiment, the sources 102, 103 and 104 may be triggered in a synchronously alternating or out-of-phase fashion at the same frequency, such that, at a given time, the detector 108 may record data corresponding to one of the first fluorescence image, the second fluorescence image and the white light image.

Further, in certain embodiments, the recorded data may be processed by the processing unit 110, for example as previously discussed with reference to FIG. 1A, for subsequent display on the display device 114 and/or for further evaluation of a pathological condition of the subject. The embodiment of the system 100 illustrated in FIG. 1B, thus, may allow for reduction in equipment cost and size. Accordingly, the system 100 may be used in not only in larger bench-top open surgical instruments, but also telescopic instruments such as an endoscope, a laparoscope and/or a handheld imaging device used during MIS procedures.

Figure 2A:
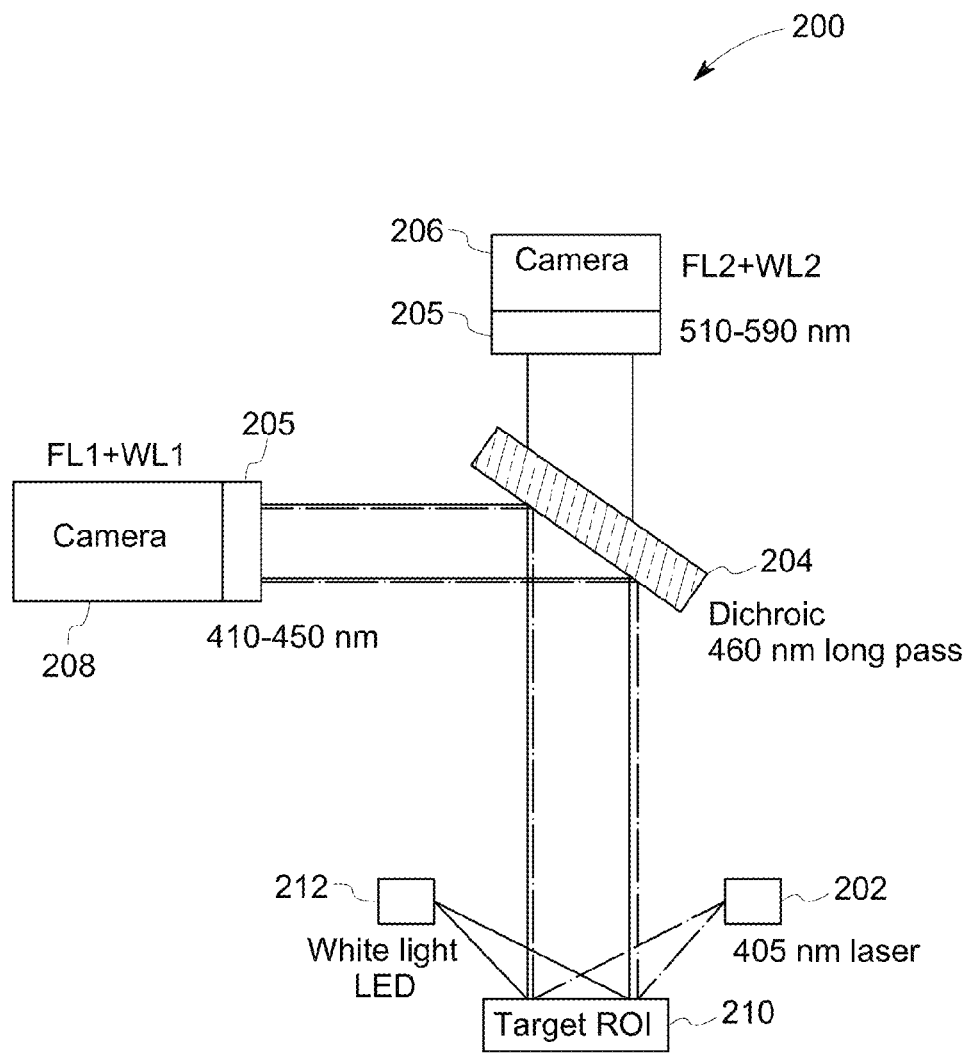
FIGS. 2A and 2B are schematic representations of exemplary configurations of imaging systems, similar to the systems illustrated in FIGS. 1A and 1B, respectively, with specific details of the system components, in accordance with aspects of the present disclosure.
Figure 2B:
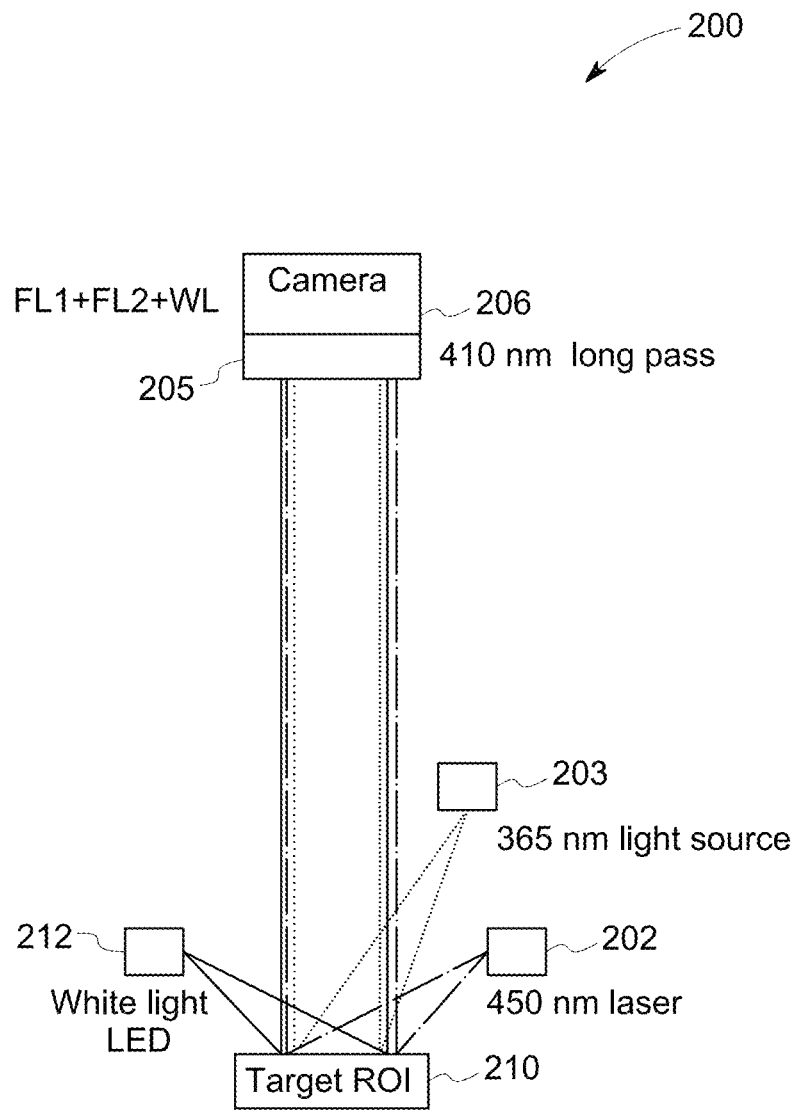

Further, FIGS. 2A and 2B illustrate exemplary configurations of an imaging system 200, similar to the system 100 of FIGS. 1A and 1B, respectively for implementing efficient data acquisition and fat-suppression procedures, in accordance with aspects of the present disclosure. In certain embodiments, the system 200 includes a single fluorescence illumination source 202, a 460 nm single-edge dichroic beam splitter 204, 410-450 nm and 510-590 nm single band interference filters 205 and a plurality of detectors 206-208 for imaging a target ROI 210 of the patient. Particularly, in one embodiment, the source 202 may include a high power laser diode configured to emit excitation light at a desired wavelength, for example of about 405 nanometer (nm), so as to allow for maximum absorption of the specific MBP imaging agent being used. The excitation light strikes the target ROI 210 and causes emission of fluorescent signals from the target ROI 210.

Further, in FIG. 2A, the dichroic beam splitter 204, for example including a 460 nm single-edge filter, may be configured to separate the fluorescence emissions into a first and a second spectral region. In one embodiment, the first spectral region corresponds to wavelengths from about 410 nm to about 450 nm, whereas the second spectral region corresponds to wavelengths from about 510 nm to about 590 nm. In accordance with an aspect of the present disclosure, the first and the second spectral regions may be selected such that one or more spectroscopic properties of a target species such as nerves and a unintentionally labeled background species such as fat differs in the two spectral regions. The emissions corresponding to the two spectral regions may be received in two emission channels and is subsequently processed to allow for discrimination between the nerve and the fat tissues in real- or near real-time, for example, as previously discussed with reference to FIG. 1A.

In certain embodiments, the system 200 may further include a white light source 212, similar to the white light source 103 of FIGS. 1A-1B. In such embodiments, the detectors 206-208 may be configured to collect corresponding white light signals reflected from the target ROI 210 along with fluorescence emissions corresponding to either the first or the second spectral region in one of the emission channels, for example, using time-domain multiplexing. In certain embodiments, the system 200 may be configured such that a time-domain multiplexing of the detectors 206-208, white light source 212 and fluorescence excitation light source 202 may be employed on both emission channels, in accordance with aspects of the present disclosure.

FIG. 2B illustrates an alternative embodiment of the imaging system 200 using single emission and multiple excitation approach for generating high fidelity fat-suppressed images. Accordingly, in the embodiment illustrated in FIG. 2B, the system 200 employs a single camera or detector 206 for collecting white light and/or fluorescence emissions. Furthermore, the system 200 may not include the single-edge dichroic beam splitter 204 illustrated in FIG. 2A. Instead, the system 200 may include two fluorescence illumination sources 202 and 203, where the illumination source 202 may be a laser diode configured to produce excitation wavelengths of about 405 nm and the source 203 may be another light source configured to produce excitation wavelengths of about 365 nm. Additionally, the system 200 of FIG. 2B may also include an emission filter and/or a notch filter 205 that may be configured to cut the excitation wavelengths and allow detection of the fluorescence emissions in the long range of wavelengths, for example using a 410 nm long pass edge filter.

Particularly, in one embodiment, use of the different excitation wavelengths may allow fluorescence emissions, for example, corresponding to single spectral bandwidth of about 410-600 nm and/or 410 nm long pass spectral bandwidth. In certain embodiments, at least two excitation wavelengths are selected such that a determined difference between fluorescence corresponding to the target species and the background species emitted in response to the first excitation wavelength differs from a corresponding difference in fluorescence emitted in response to the second excitation wavelength. Further, the system 200 may employ time-domain multiplexing to allow the detector 206 to collect the fluorescence emissions corresponding to the first and second excitation wavelengths in a time-interleaved manner from alternating frames.

In certain embodiments, the system 200 may further include the white light source 212 for imaging the target ROI.

Accordingly, the system 200 may employ time-domain multiplexing of the single emission channel to collect the fluorescence emissions corresponding to the first and the second excitation wavelengths and white light alternately one after the other in three consequent frames. To that end, the sources 202, 203 and 212 may be triggered in a synchronously alternating or out-of-phase fashion at the same frequency, such that, at a given time, the detector 206 may record data corresponding to one of the first fluorescence image, the second fluorescence image and the white light image.

As previously discussed with reference to FIG. 1A, in certain embodiments, the recorded data may be processed, for example using the processing unit 110 of FIGS. 1A-1B, for reconstruction of fat-suppressed images for subsequent display and/or analysis. Use of the fat-suppressed images may allow for real-time tissue characterization during open and/or MIS surgeries.

Generally, fluorescence images may provide additional functional information through auto fluorescence of endogenous NADH, flavin adenine dinucleotide (FAD), elastins, collagens, or porphyrins useful during surgical procedures. However, during MIS procedures, real-time surgical guidance is of great significance for preventing iatrogenic nerve damage and/or for providing indicating information about dynamic processes, such as relating to change in imaging agent concentration, evolving in the target ROI 210 of the patient. White light images may provide navigational cues for aiding in real-time guidance during surgical procedures. Accordingly, in certain embodiments, the system 200 may benefit from a dedicated white light or red-green-blue (RGB) emission channel (not shown in FIG. 2A-2B).

Figure 3:
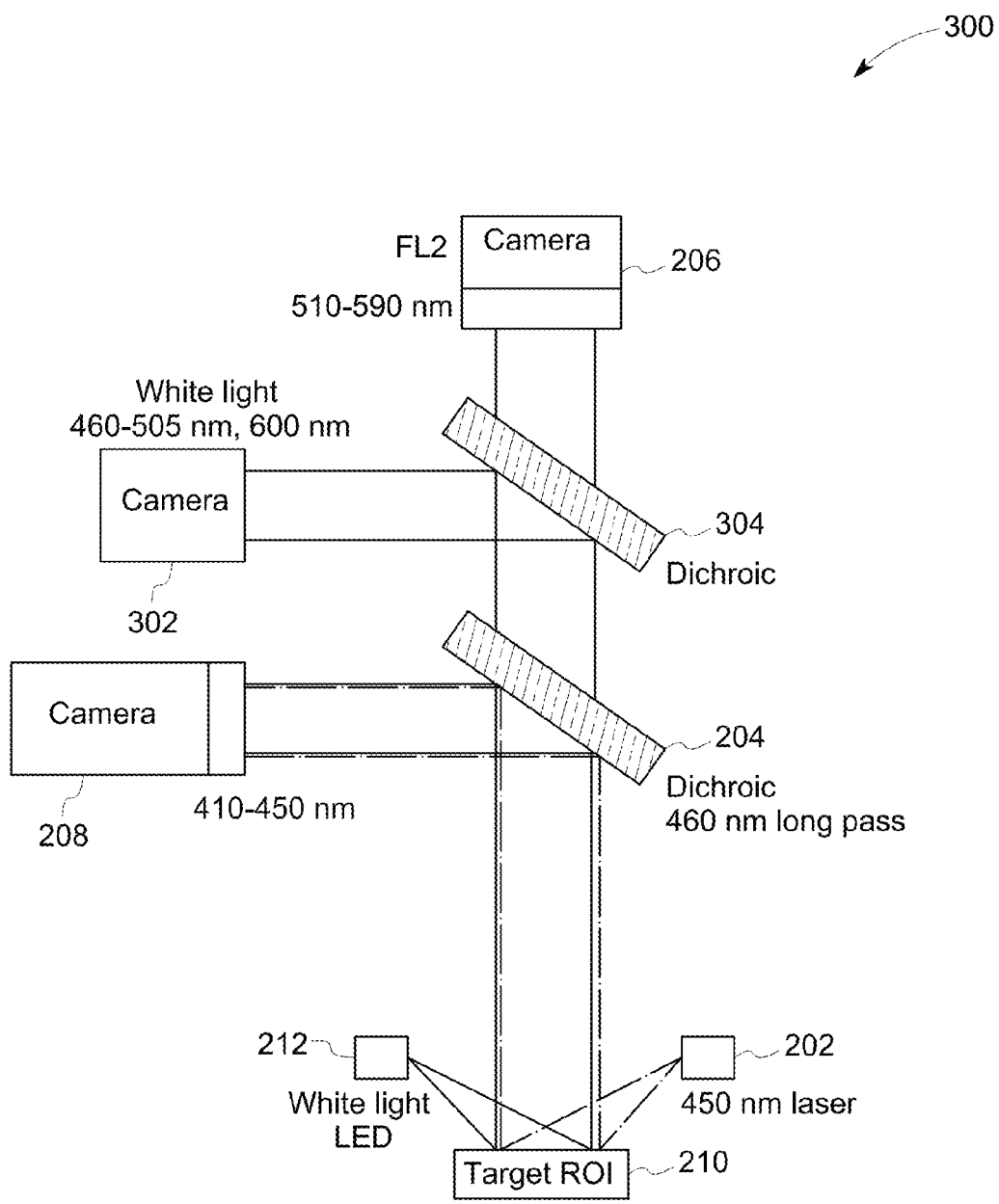
FIG. 3 is a schematic representation of an alternative embodiment of the system of FIG. 2A including a dedicated white light camera, in accordance with aspects of the present disclosure.

FIG. 3 illustrates an exemplary embodiment of the system 300, similar to system 200 of FIG. 2A, where the system 300 includes the white light source 212 of FIG. 2A and a dedicated white light camera 302 configured to detect wavelengths, for example, of about 460-505 nm—, or about 600 nm. Although, FIG. 3 depicts a separate white light source 212, in certain embodiments, a single illumination source configured to produce different excitation wavelengths capable of producing fluorescence in an imaging agent, while also allowing for white light and/or color imaging may be used. For discussion purposes, the embodiment illustrated in FIG. 3 depicts a separate white light source 212 used in concert with the fluorescence illumination source 202, the dichroic filter 204 and at least two detectors 206-208, as described with reference to FIG. 2A.

Further, in one embodiment, the white light source 212 may include an LED configured to produce excitation light for use in generating white light and/or color images. The white light source 212 may be configured to operate under computer control, external trigger from an associated processing subsystem, such as the processing unit 110 of FIGS. 1A-1B and/or based on user input for generating white light images. Moreover, in certain embodiments, the white light source 212 may be configured to generate white light corresponding to a wavelength different from the wavelengths in the first and second spectral regions used for fluorescent imaging.

As previously noted, in one embodiment, the excitation light generated by the fluorescence illumination source 202 causes fluorescence emissions from the target ROI 210. The fluorescence emissions, separated into the first and second spectral region, are collected by the detectors 206-208 using the first and the second emission channels. The collected signals corresponding to the first and second spectral region may then be used to generate fat-suppressed images, as described with reference to FIG. 1A, in accordance with an aspect of the present disclosure.

Additionally, the light emitted from the target ROI 210 in response to the white light generated by the white light source 212 may be collected by the dedicated white light camera 302. The collected white light signals may be transmitted to the processing unit 110 for reconstructing white light images. Further, in certain embodiments, composite white light images may be generated based on relative contributions from each of the detectors 206-208, for example, corresponding to spectral regions 410-450 nm and 510-590 nm.

Use of the dedicated white light channel in addition to multiple fluorescence emission channels allows for minimizing impact of spectral overlapping between fluorescence and white light channels, thus obtaining high fidelity images on all three channels. As previously noted, in certain embodiments, the high fidelity white light images may be displayed on a display along with the raw and/or fat-suppressed fluorescence images over a common spatial coordinate system for use in diagnosis and/or device navigation.

Figure 4:
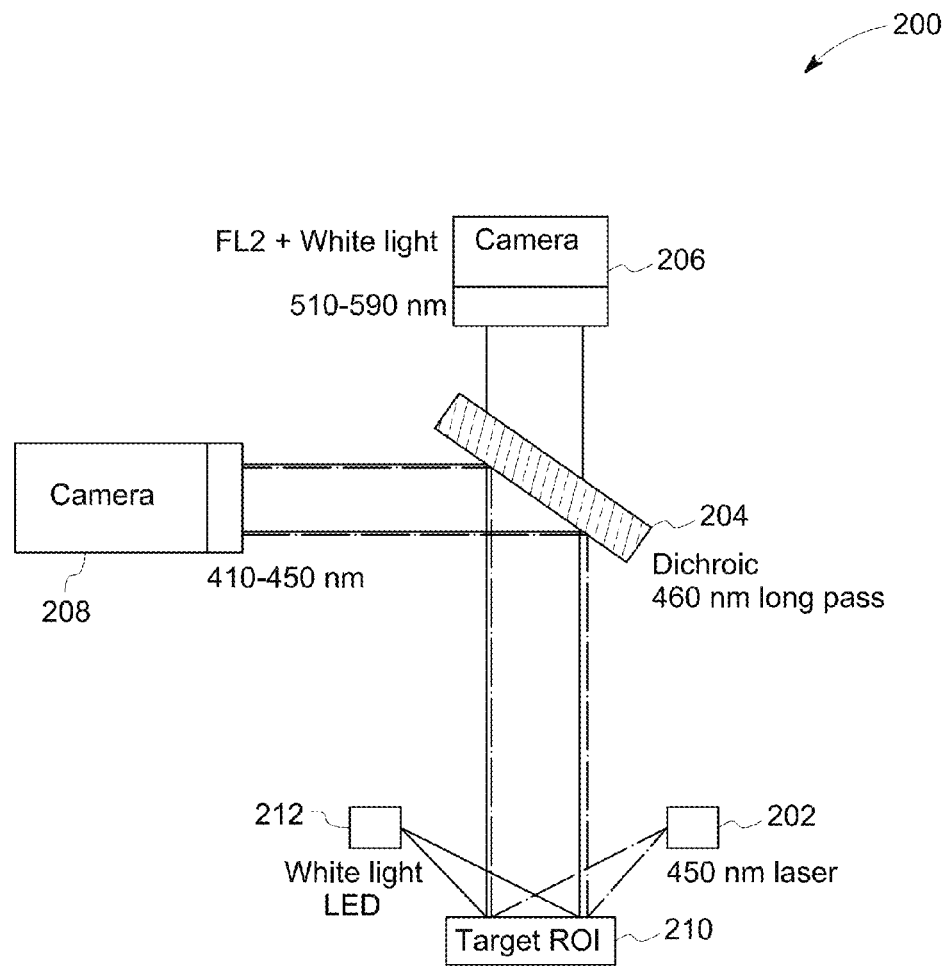
FIG. 4 is a schematic representation of another embodiment of the system of FIG. 2A, where white light and one of the fluorescence images are collected on one emission channel via a time-domain multiplexing method, in accordance with aspects of the present disclosure.

In contrast to the embodiment illustrated in FIG. 3 that depicts use of the dedicated white light camera 302, FIG. 4 illustrates an exemplary embodiment of the system 200 of FIG. 2A that may be configured to implement one or more white light channels without use of a dedicated white light camera. To that end, the system 200 may employ, for example, a time interleaved detection/illumination scheme. Particularly, the system 200 may be configured to use time-domain multiplexing on one of the emission channels for capturing white light and fluorescent images in alternative frames. By way of example, in one embodiment, the system 200 may be configured to capture a white light image and a fluorescent image corresponding to the second spectral region from the second detector 208 in alternative frames using synchronized laser and white light illumination. In this embodiment, the first detector 206 may be configured to collect fluorescence emissions corresponding to only the first spectral region. The two fluorescent images may then be processed, as described with reference to FIG. 1A, for reconstructing fat-suppressed images of the target ROI.

Figure 5:
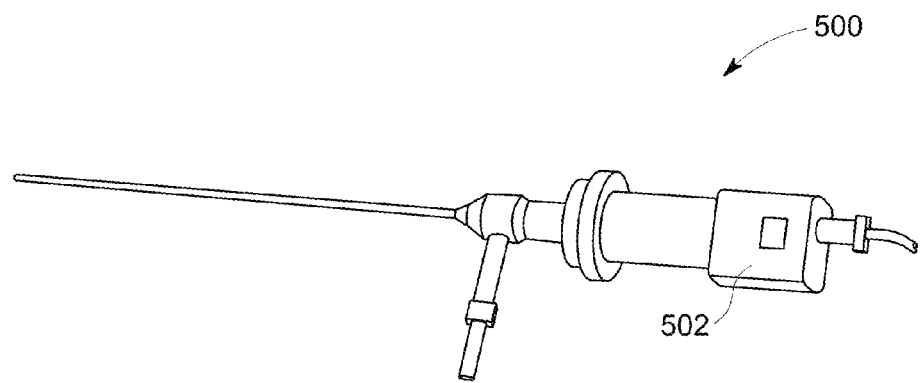
FIG. 5 is an illustration of an exemplary embodiment of a minimally-invasive laparoscope employing a triple mode camera, in accordance with aspects of the present disclosure.

Further, FIG. 5 illustrates an exemplary embodiment of a minimally-invasive laparoscope 500, which is similar to the system 200 illustrated in FIG. 2B and is configured to employ time-domain multiplexing of a single emission channel. To that end, the laparoscope 500 may include a single triple mode camera 502 configured to collect three images, for example, two fluorescence and one white light image in a single emission channel using time-domain multiplexing.

Figure 6:
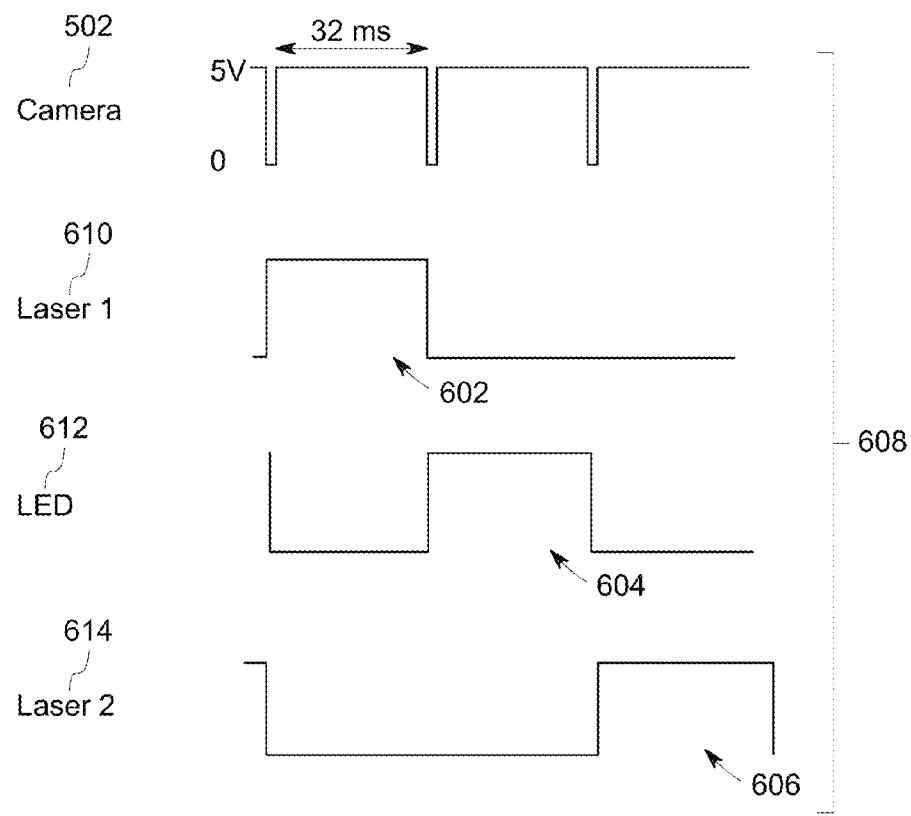
FIG. 6 is an illustration of an example of a time-multiplexing method for use by the triple mode camera of FIG. 5, in accordance with aspects of the present disclosure.

FIG. 6 illustrates an example of a time-domain multiplexing method that may be employed by the triple mode camera 502 of FIG. 5 for collecting three images in three different time slots 602, 604 and 606 in a single emission channel 608. Particularly, in one embodiment, the camera 502 may be configured to acquire the fluorescence emissions corresponding to excitation light emitted from a first laser light source 602 in the first time slot 602 for generating the first fluorescence image. Further, the camera 502 may collect white light from an LED 612 in the second time slot 604 and fluorescence emissions corresponding to excitation light emitted from a second laser light source 614 from the third time slot 606 in a time interleaved manner for generating the white light and the second fluorescence image, respectively.

Use of the triple mode camera 502, thus allows for efficient data acquisition from the different illumination sources 610-614. The efficient data acquisition, in turn, may allow for reconstruction of fluorescence and/or white light images at a near video rate, such that the images may be displayed in real time. To that end, the two light sources 202 and 302 may be triggered in a synchronously alternating or out-of-phase fashion at the same frequency, such that, at a given time, the detector may record one of the first fluorescence image, the second fluorescence image and the white light image. Certain exemplary methods for generating fat-suppressed images in accordance with aspects of the present disclosure will be described in greater detail with reference to FIG. 7.

Figure 7:
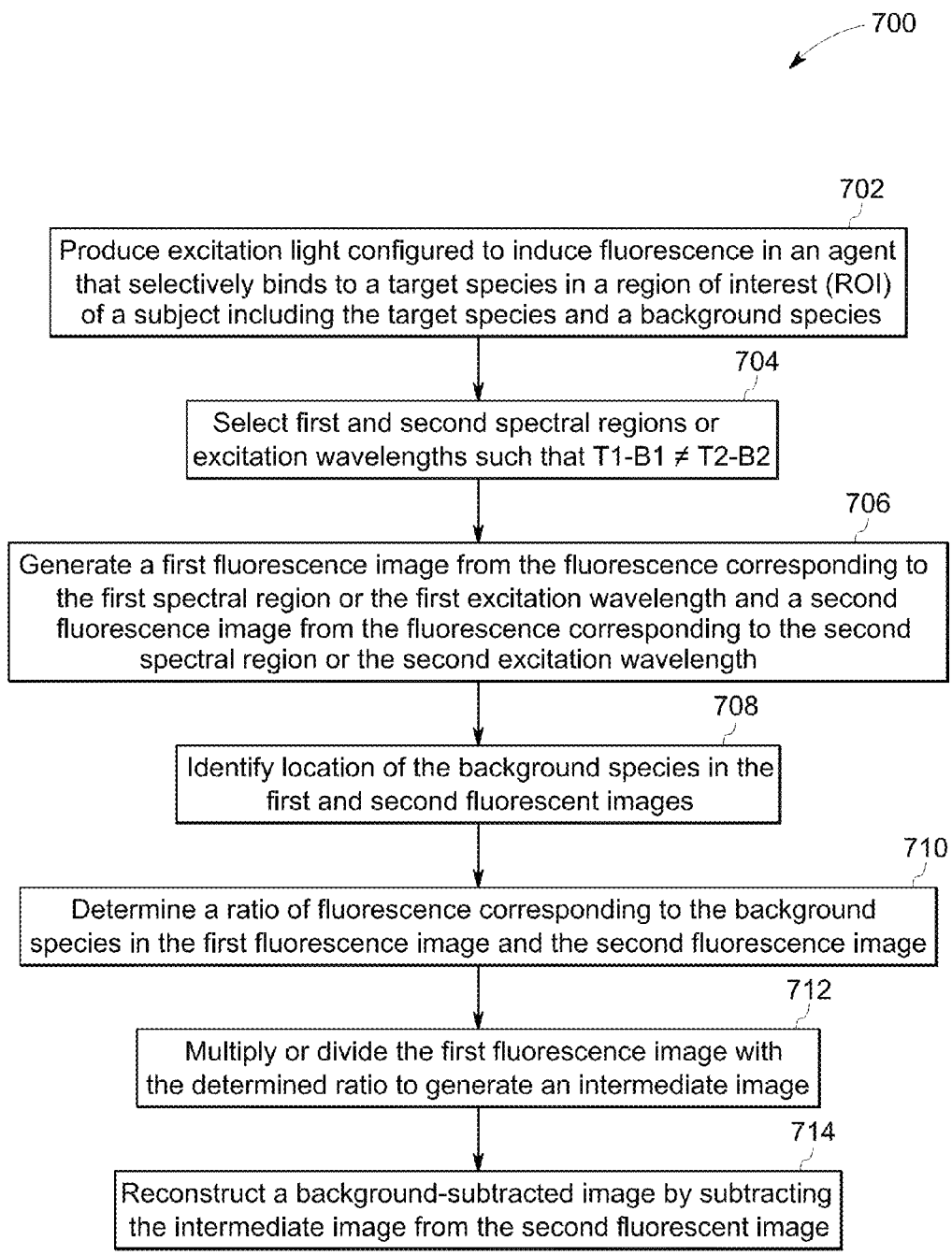
FIG. 7 is a flowchart depicting an exemplary method for imaging, in accordance with aspects of the present disclosure.

FIG. 7 illustrates a flow chart 700 depicting an exemplary method for imaging a target ROI of a patient. The exemplary method may be described in a general context of computer executable instructions stored and/or executed on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 7, the exemplary method is illustrated as a collection of blocks in a logical flow chart, which represents operations that may be implemented in hardware, software, or combinations thereof. The various operations are depicted in the blocks to illustrate the functions that are performed, for example, during fluorescence image generation, ratio determination and image reconstruction phases of the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-6.

As previously noted, surgical procedures, including MIS may cause iatrogenic damage. Accordingly, clinically there is a significant demand to enhance the capabilities of surgical devices, specifically MIS devices, through the integration of in situ, in vivo functional capabilities to provide improved tissue characterization and targeting at both macro and cellular levels. One of the recent advances in biophotonics for MIS is the introduction of fluorescence imaging for real-time tissue characterization. As MIS aids in reducing patient trauma, improving therapeutic outcome and/or faster post-operative recovery, MIS is increasingly used in various surgical procedures.

For example, during laparoscopic prostatectomy, a laparoscope may be inserted through small incisions to allow surgeons to visualize inside the abdomen and perform the surgery. However, despite measures to spare nerves during MIS, nerve damage commonly occurs. Often, the nerve damage is a result of unintentional labeling of a background species such as fat tissues by an imaging agent, which leads to inaccurate images. Given the emerging utility of MIS in various surgical scenarios, and a persistently high incidence of complications from nerve damage, surgery outcomes may be improved through high-fidelity fat-suppressed fluorescence imaging of nerves using embodiments of the present method.

To that end, at step 702, excitation light configured to induce fluorescence emissions in an imaging agent that selectively binds to MBP applied to a ROI of a subject may be produced, where the ROI includes a target species and a background species. In one embodiment, the target species includes nerve tissues and the background species includes fat tissues. Moreover, as previously noted, in one embodiment, the imaging agent may include a compound of Formula I, although alternative embodiments may employ other suitable imaging agents.

In certain embodiments, where an associated imaging system, such as the system 200 of FIG. 2A, includes a single excitation, multiple emission approach, the excitation light may be generated using a single fluorescence illumination source, such as the source 202 of FIG. 2A. In such an embodiment, the system 200 may further include a dichroic beam splitter, for example the dichroic filter 204 of FIG. 2A, configured to separate the fluorescence emissions received from the target ROI in response to the excitation light into first and second spectral regions.

However, in embodiments, where the imaging system, such as the system 200 of FIG. 2B, employs a single emission, multiple excitation approach, more than one illumination source may be employed to produce at least two excitation wavelengths for inducing fluorescence emissions corresponding to a first excitation wavelength and a second excitation wavelength in the imaging agent.

As previously noted with reference to both FIGS. 2A-2B, at step 704, the first and the second spectral regions and/or excitation wavelengths may be selected such that a determined difference between fluorescence corresponding to the target species and the background species emitted in response to the first excitation wavelength or corresponding to the first spectral region differs from a corresponding difference in fluorescence corresponding to the second excitation wavelength or second spectral region. In accordance with an aspect of the present disclosure, the difference in spectroscopic properties, for example, fluorescence of the target species such as nerves and an unintentionally labeled background species such as fat in the two spectral regions may be used for differentiating between the nerve and fat tissues more reliably.

Additionally, in certain embodiments, the system 200 may also include a white light source for providing white and/or visible light illumination. Particularly, in one embodiment, the system 200 may employ a dedicated white light camera and/or use time-domain multiplexing of one or more emission channels to allow collection of both white light and fluorescent images for use in real-time device tracking and/or diagnosis.

Further, at step 706, a first fluorescence image may be generated from the fluorescence emissions corresponding to the first spectral region or the first excitation wavelength and a second fluorescence image may be generated from the fluorescence emissions corresponding to the second spectral region or the second excitation wavelength. Additionally, at step 708, location of the background species such as unintentionally labeled fat tissue may be identified in the first and second fluorescent images. As previously noted, in one embodiment, the location of the fat tissues may be identified through an automated analysis of the fluorescence images. Alternatively, the fat tissues may be identified through user input, for example, received via a GUI indicating the background species in the first and second fluorescent images displayed on a display, such as the display device 114 of FIG. 1.

Further, at step 710, a ratio of fluorescence corresponding to the fat tissues identified in the first and the second fluorescence images may be determined. At step 712, the first fluorescence image may be multiplied or divided with the determined ratio to generate an intermediate image. In one embodiment, the intermediate image may correspond to a fluorescence image that includes a substantially similar amount of fat as present in the second fluorescence image. Subsequently, at step 714, a background-subtracted image may be reconstructed by subtracting the intermediate image from the second fluorescence image.

Since the multiplication or division operation described in step 712 leads to equalization of fat in the intermediate and the second fluorescence images, in one embodiment, the subsequent subtraction operation of step 714 cancels out the fat tissues in the resulting image. The background-subtracted image, thus, exhibits high nerve-to-fat ratio by substantially eliminating the unintentionally labeled fat tissues, while improving visualization of the targeted nerve tissues. Such high quality fat-suppressed images may be used for medical diagnosis, prescribing treatment, and/or for device tracking in real-time during MIS procedures with greater reliability.

Figure 8A:
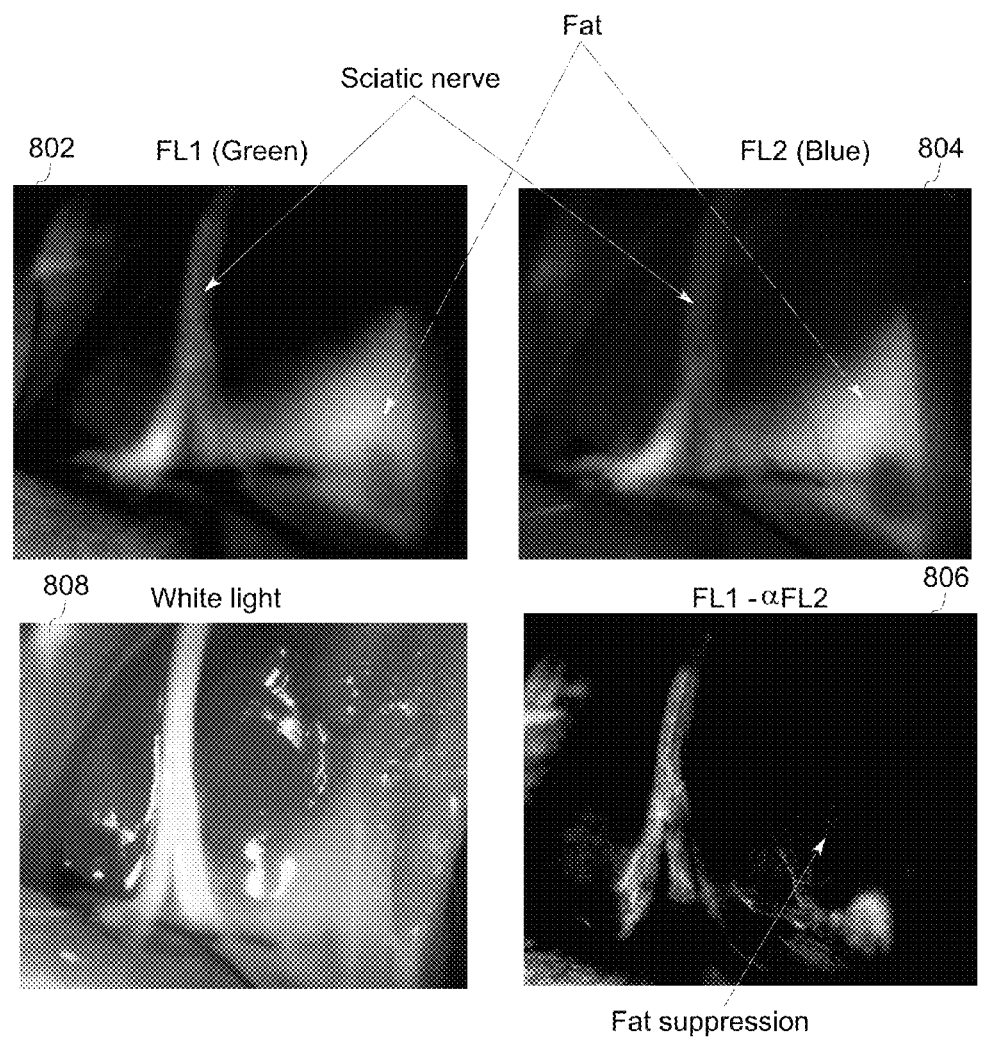
FIGS. 8A and 8B are illustrations of images generated using the exemplary method of FIG. 7 implemented by the exemplary systems illustrated in FIGS. 1A and 1B, respectively, in accordance with aspects of the present disclosure.
Figure 8B:
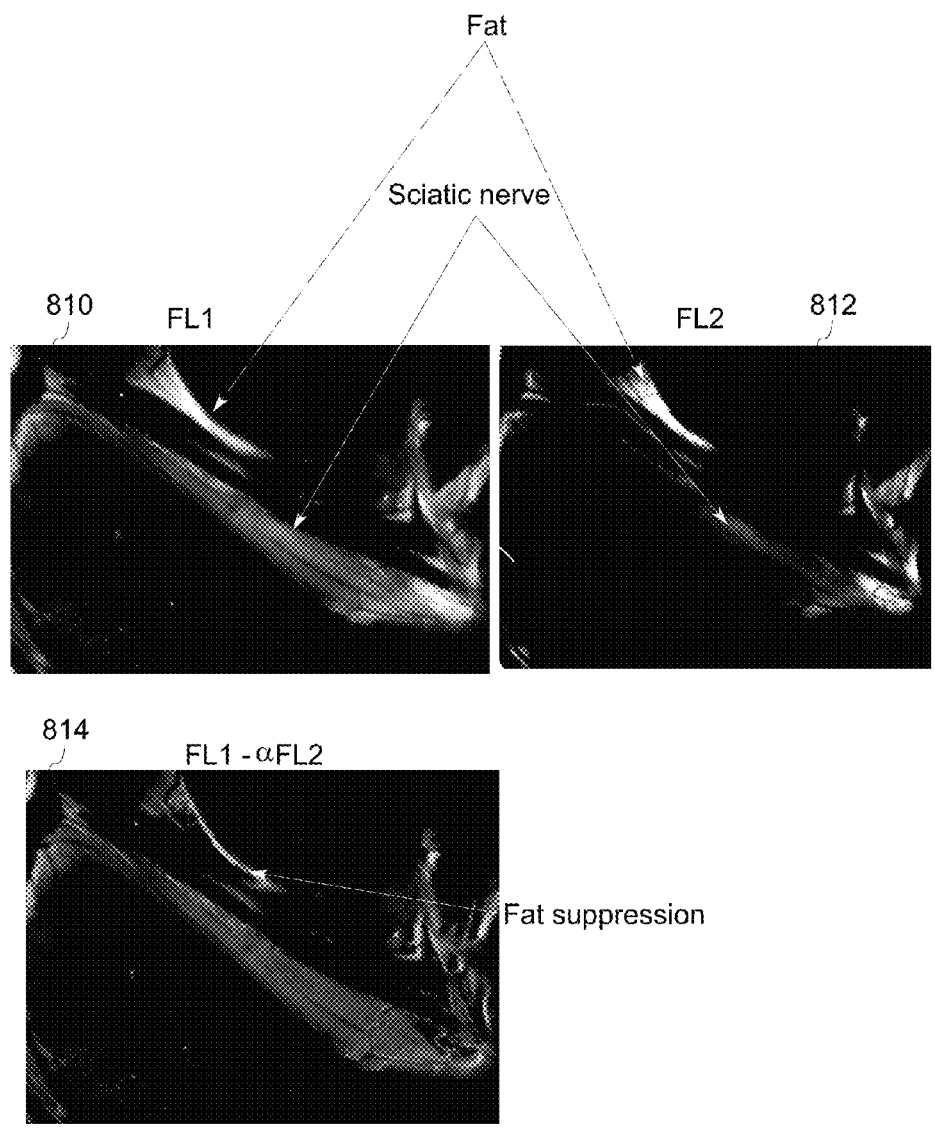

Certain images generated using an exemplary implementation of the present method described with reference to FIG. 7 and implemented by embodiments of the system 100 depicted in FIGS. 1A and 1B are illustrated in FIGS. 8A and 8B, respectively. Particularly, FIG. 8A illustrates raw fluorescence images 802 and 804 generated using emission signals corresponding to the first and the second spectral region, respectively. FIG. 8A also illustrates a white light image 806 of the target ROI generated using the system 100 of FIG. 1A. FIG. 8A further illustrates a fat-suppressed image 808 generated using an embodiment of the present method, such as described with reference to FIG. 7. As illustrated in FIG. 8, both the raw fluorescence images 802, 804 and the white light image 806 show sufficient nerve visualization, although the fat tissues are visualized with even higher contrast due to unintentional binding of the imaging agent.

It may be noted that, in the exemplary implementation, raw fluorescence images corresponding to the first and second spectral regions or excitation wavelengths were acquired using a color camera. The acquired images were separated into Red-Green-Blue (RGB) channels. Specifically, the images were split to generate the first fluorescence image 802 on the green channel corresponding to the wavelengths 510-590 nm in the first spectral region or the first excitation wavelength and the second fluorescence images 804 on the blue channel corresponding to the wavelengths 410-450 nm in the second spectral region or the second excitation wavelength.

Although a color camera was used in the present implementation, an alternative embodiment may employ a monochrome camera. The raw fluorescence images generated by the monochrome camera may then be used directly for generating fat-suppressed images. Use of the digital solution described with reference to steps 702-712 of FIG. 7 for processing the raw fluorescent images 802 and 804, thus, allowed for automated generation of fat-suppressed images 808 for use during surgery in real-time. In certain embodiments, the digital solution may provide clean fluorescence images including only the nerve tissue.

Similarly, FIG. 8B illustrates raw fluorescence images 810 and 812 generated using emission signals corresponding to the first and the second excitation wavelengths, respectively. FIG. 8B further illustrates a fat-suppressed image 814 generated using a digital solution, such as described with reference to FIG. 7. As illustrated in FIG. 8B, the fat tissues were substantially suppressed in the image 814 as compared to the raw fluorescence images 810 and 812.

Particularly, in the exemplary implementation, the digital solution provided significant improvements in nerve-to-fat ratio at a low power level (for example, about 54 mW), at a medium power level (for example, about 69 mW) and at a high power level (for example, about 76 mW). Such improvement in nerve visualization regardless of the power levels is because, in the digital solution, the signal in any of the channels may be digitally scaled by a certain number to make the fat signal the same in the two channels. As previously noted, the ratio between fat in the two raw fluorescence images corresponding to different spectral regions may be used as an efficient scaling factor for efficient fat suppression in the resulting images.

Use of embodiments of systems and methods of the present disclosure, thus, allow for generation of high-fidelity fat-suppressed images in real-time during a medical procedure. The high-fidelity real-time images aid the medical practitioner in making accurate assessments regarding patient pathology, while also providing reliable navigational cues during MIS procedures. As previously noted, embodiments of the present disclosure allow for efficient fat suppression using automated digital means regardless of the power levels. The efficient fat suppression enhances efficiency of fluorophores that specifically label biological targets and have favorable biological and chemical properties, but may have been eliminated earlier from the development pipeline owing to inadequate SBR.

Particularly, both the single excitation, multiple emission approach and the single emission, multiple excitation approach provide efficient acquisition and fat-suppression procedures that may be implemented in both a bench-top open surgical instrument and a compact, hand-held and/or minimally-invasive device. Additionally, use of a white light channel allows for generation of white light and/or color images for use in real-time navigation. Moreover, in both approaches, use of time-domain multiplexing for collecting the white light and fluorescent images substantially simultaneously aids in reducing system size and associated costs, thus making implementation of the present methods and systems in small minimally-invasive devices feasible.

Although specific features of various embodiments of the present systems and methods may be shown in and/or described with respect to only certain drawings and not in others, this is for convenience only. It is to be understood that the described features, structures, and/or characteristics may be combined and/or used interchangeably in any suitable manner in the various embodiments, for example, to construct additional assemblies and techniques. Furthermore, the foregoing examples, demonstrations, and process steps, for example, those that may be performed by the processing unit 110 may be implemented by a single device or a plurality of devices using suitable code on a processor-based system.

It should also be noted that different implementations of the present disclosure may perform some or all of the steps described herein in different orders or substantially concurrently, that is, in parallel. In addition, the functions may be implemented in a variety of programming languages, including but not limited to Python, C++, Java and/or Labview. Such code may be stored or adapted for storage on one or more tangible, machine-readable media, such as on data repository chips, local or remote hard disks, optical disks (that is, CDs or DVDs), solid-state drives or other media, which may be accessed by a processor-based system to execute the stored code.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging system, comprising:
   one or more illumination sources configured to produce excitation light that induces fluorescence emissions in an imaging agent configured to bind to a target species in a region of interest of a subject, wherein the region of interest comprises the target species and a background species;
   at least one optical element configured to separate the fluorescence emissions into a first spectral region and a second spectral region, wherein a determined difference between fluorescence corresponding to the target species and the background species in the first spectral region differs from a corresponding difference in the second spectral region;
   one or more signal detectors configured to collect fluorescence emissions corresponding to the first spectral region and the second spectral region; and
   a processing unit operatively coupled to the one or more signal detectors, wherein the processing unit is configured to:
      generate a first fluorescence image from the fluorescence emissions corresponding to the first spectral region and a second fluorescence image from the fluorescence emissions corresponding to the second spectral region;
      determine a ratio of fluorescence corresponding to the background species in the first fluorescence image and the second fluorescence image;
      multiply or divide the first fluorescence image with the determined ratio to generate an intermediate image; and
      reconstruct a background-subtracted image by subtracting the intermediate image from the second fluorescence image.

2. The system of claim 1, comprising a single illumination source configured to excite fluorescence in one or more of the imaging agent and the region of interest of the subject.

3. The system of claim 1, further comprising a display operatively coupled to the processing unit and configured to display the first fluorescence image, the second fluorescence image, the intermediate image, the background-subtracted image, or combinations thereof.

4. The system of claim 1, wherein the target species corresponds to nerve tissue and the background species corresponds to adipose tissue.

5. The system of claim 1, further comprising a white light illumination source.

6. The system of claim 5, wherein the fluorescence corresponding to the first spectral region is emitted in a first fluorescence emission channel, the fluorescence corresponding to the second spectral region is emitted in a second fluorescence emission channel and white light is emitted in a dedicated white light channel.

7. The system of claim 5, wherein the white light illumination source and the one or more illumination sources configured to produce excitation light that induces fluorescence are synchronized with one or more of a first detector and a second detector in the one or more detectors, and wherein one or more of the first detector and the second detector are configured to alternatingly collect a white light, the fluorescence emissions corresponding to the first spectral region and the fluorescence emissions corresponding to the second spectral region.

8. The system of claim 7, wherein the processing unit uses fluorescence emissions collected from a first fluorescence emission channel and a second fluorescence emission channel for spectral discrimination between nerve tissue and adipose tissue.

9. The system of claim 1 implemented in a minimally-invasive instrument, wherein the minimally-invasive instrument comprises one or more of a laparoscope and a flexible endoscope.

10. The system of claim 1, wherein the imaging agent that selectively binds to the target species comprises a compound of Formula I, and wherein Formula I is represented as:

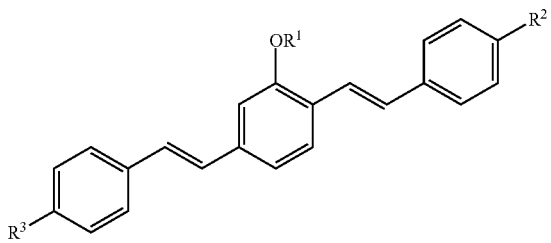

wherein $R^1$ is an alkyl group, and $R^2$ is an electron donating group and $R^3$ is an electron withdrawing group or $R^2$ is an electron withdrawing group and $R^3$ is an electron donating group.

11. A system for nerve imaging, comprising:
   one or more illumination sources configured to produce at least a first excitation wavelength and a second excitation wavelength for inducing fluorescence emissions in an imaging agent that selectively binds to a target species in a region of interest of a subject,
      wherein the region of interest comprises the target species and a background species, and
      wherein the first excitation wavelength and the second excitation wavelength are selected such that a determined difference between fluorescence corresponding to the target species and the background species emitted in response to the first excitation wavelength differs from a corresponding difference in fluorescence emitted in response to the second excitation wavelength;
   one or more signal detectors configured to collect the fluorescence emitted in response to the first excitation wavelength and the second excitation wavelength;
   a processing unit operatively coupled to the one or more signal detectors, wherein the processing unit is configured to:
      generate a first fluorescence image from the fluorescence emitted in response to the first excitation wavelength and a second fluorescence image from fluorescence emitted in response to the second excitation wavelength;
      determine a ratio of fluorescence corresponding to the background species in the first fluorescence image and the second fluorescence image;
      multiply or divide the first fluorescence image with the determined ratio to generate an intermediate image; and
      reconstruct a background-subtracted image by subtracting the intermediate image from the second fluorescence image.

12. The system of claim 11, wherein the fluorescence emitted in response to the first excitation wavelength and the fluorescence emitted in response to the second excitation wavelength are emitted in a single emission channel.

13. The system of claim 12, wherein the one or more illumination sources are synchronized with the at least one of the signal detectors, and wherein the at least one of the signal detectors is configured to alternatingly collect a white light, the fluorescence emitted in response to the first excitation wavelength and the fluorescence emitted in response to the second excitation wavelength using time-domain multiplexing of the single emission channel.

14. The system of claim 11, implemented in a minimally-invasive instrument, wherein the minimally-invasive instrument comprises one or more of a laparoscope and a flexible endoscope.

15. The system of claim 11, wherein the imaging agent that selectively binds to the target species comprises a compound of Formula I, and wherein Formula I is represented as:

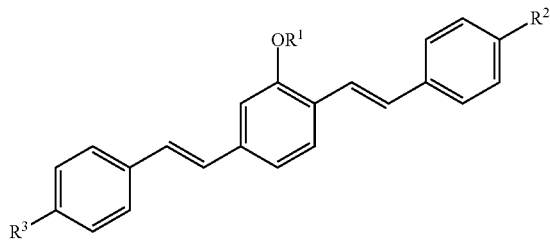

wherein $R^1$ is an alkyl group, and $R^2$ is an electron donating group and $R^3$ is an electron withdrawing group or $R^2$ is an electron withdrawing group and $R^3$ is an electron donating group.

16. A method for imaging, comprising:

producing excitation light configured to induce fluorescence emissions in an imaging agent that selectively binds to myelinated nerves in a region of interest of a subject, wherein the region of interest comprises a target species and a background species;

selecting a first spectral region and a second spectral region such that a determined difference between fluorescence corresponding to the target species and the background species in the first spectral region differs from a corresponding difference in the second spectral region;

generating a first fluorescence image from the fluorescence emissions corresponding to the first spectral region and a second fluorescence image from the fluorescence emissions corresponding to the second spectral region;

determining a ratio of fluorescence corresponding to the background species in the first fluorescence image and the second fluorescence image;

multiplying or dividing the first fluorescence image with the determined ratio to generate an intermediate image; and reconstructing a background-subtracted image by subtracting the intermediate image from the second fluorescent image.

\* \* \* \* \*